United States Patent [19]
Martel et al.

[11] 4,273,727
[45] Jun. 16, 1981

[54] (S) α-CYANO-3-PHENOXY-BENZYL ALCOHOL

[75] Inventors: Jacques Martel, Bondy; Jean Tessier, Vincennes; André Teche, Nanterre; Jean-Pierre Demoute, Montreuil-sous-Bois, all of France

[73] Assignee: Roussel Uclaf, Paris, France

[21] Appl. No.: 973,791

[22] Filed: Dec. 28, 1978

[30] Foreign Application Priority Data

Jan. 31, 1978 [FR] France ............... 78 02621

[51] Int. Cl.³ .................................. C07C 121/75
[52] U.S. Cl. .................. 260/465 F; 260/343.3 R; 260/465 D
[58] Field of Search ......... 260/465 F, 343.21, 343.3 R

[56] References Cited

U.S. PATENT DOCUMENTS

| | | | |
|---|---|---|---|
| 3,723,469 | 3/1973 | Martel | 260/343.3 |
| 3,922,286 | 11/1975 | Yoshioka et al. | 260/343.2 |
| 3,989,654 | 11/1976 | Honda et al. | 260/343.21 |
| 4,014,918 | 3/1977 | Martel | 260/343.21 |
| 4,133,826 | 1/1979 | Warnant et al. | 260/465 D |

OTHER PUBLICATIONS

Ruzo et al., J. Agric. Food Chem., vol. 25, pp. 1385–1394 (1977).
Ruzo et al., Tetrahedron Letters, No. 35, pp. 3045–3048 (1976).

Primary Examiner—Dolph H. Torrence
Attorney, Agent, or Firm—Hammond & Littell, Weissenberger and Muserlian

[57] ABSTRACT (S) α-cyano-3-phenoxy-benzyl alcohol having the formula

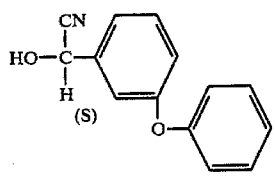

and a novel process for its preparation and novel intermediates.

2 Claims, No Drawings

(S) α-CYANO-3-PHENOXY-BENZYL ALCOHOL

STATE OF THE ART (R,S) α-cyano-3-phenoxy-benzyl alcohol which is a racemic mixture is known but until now, there has been no description of (S) α-cyano-3-phenoxy-benzyl alcohol or any method of obtaining the same.

There are procedures known for resolution of alcohols containing asymetrical carbons. For example, it is known to resolve certain (R,S) racemic alcohols by esterifying the same with an optically active organic acid and separating by physical treatment the ester of the (S) alcohol and the ester of the (R) alcohol and then individually hydrolyzing the two esters to obtain alcohols of the (R) structure and the (S) structure.

Another known, very complicated procedure consists of reacting the racemic alcohol with an organic diacid to form a hemiester which is then reacted with an optically active base to form the salts thereof which are then physically separated to obtain the salt of the optically active base and of the hemiester of the (R) alcohol and the salt of the optically base and of the hemiester of the (S) alcohol and the salts are acidified to form the free hemiesters of the (R) and (S) alcohols which are then hydrolyzed to individually obtain the (S) alcohol and the (R) alcohol.

The known methods for the resolution of racemic mixtures of alcohols have as an intermediate step the formation of esters of the alcohols and in the final step of the resolution, it is necessary to hydrolyze the ester to obtain the desired resolved alcohol. In the case of α-cyano-3-phenoxy-benzyl alcohol, the hydrolysis of the esters in acid or basic media does not lead to the desired resolved alcohol but to degradation products thereof, especially 3-phenoxy-benzaldehyde and 2-hydroxy-2-(3-phenoxyphenyl)-acetic acid. Therefore, until now, there was no known method for resolving racemic mixtures to obtain (S) α-cyano-3-phenoxy-benzyl alcohol.

OBJECTS OF THE INVENTION

It is an object of the invention to provide, for the first time, (S) α-cyano-3-phenoxy-benzyl alcohol free of its (R) form.

It is another object of the invention to provide a novel process for the preparation of (S) α-cyano-3-phenoxy-benzyl alcohol and to novel intermediates produced thereby.

These and other objects and advantages of the invention will become obvious from the following detailed description.

THE INVENTION

The novel product of the invention is (S) α-cyano-3-phenoxy-benzyl alcohol of the formula

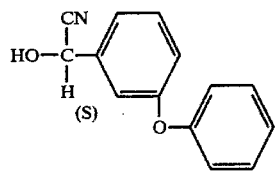

which has a negative specific rotation which is a value of about $-16.5°\pm1.5°$ when measured at a concentration of 0.8% in benzene. The process of the invention for the preparation of (S) α-cyano-3-phenoxy-benzyl alcohol includes preparing an optically active intermediate ether, namely (1R, 5S) 6,6-dimethyl-4(R)-[(S)-cyano-(3'-phenoxybenzyl)-methoxy]-3-oxa-bicyclo (3,1,0)-hexan-2-one which contrary to the classic esters used for resolution of alcohols possesses a structure which when hydrolyzed under acid conditions gives the desired alcohol in good yields. The invention also permits access to (R) α-cyano-3-phenoxy-benzyl alcohol by hydrolysis of the corresponding optically active ether.

The novel process of the invention for the preparation of (S) α-cyano-3-phenoxy-benzyl alcohol comprises reacting in the presence of an acid agent (R,S) α-cyano-3-phenoxy-benzyl alcohol with the lactone of cis 2,2-dimethyl-3S-(dihydroxymethyl)-cyclopropane-1R-carboxylic acid to obtain a mixture of (1R,5S) 6,6-dimethyl-4(R)-[(S)-cyano-(3'-phenoxyphenyl)-methoxy]-3-oxa-bicyclo-(3,1,0)-hexan-2-one and (1R,5S) 6,6-dimethyl-4(R)-[(R)-cyano-(3'-phenoxyphenyl)-methoxy]-3-oxa-bicyclo-(3,1,0)-hexan-2-one, separating the two isomers by physical means and hydrolyzing (1R,5S) 6,6-dimethyl-4(R)-[(S)-cyano-(3'-phenoxyphenyl)-methoxy]-3-oxa-bicyclo-(3,1,0)-hexan-2-one in an acid media to obtain (S) α-cyano-3-phenoxy-benzyl alcohol.

The acid agent present in the reaction of the racemic alcohol and the lactone is preferably selected from the group consisting of p-toluene sulfonic acid, methane sulfonic acid, perchloric acid, m-nitrobenzene sulfonic acid, 5-sulfosalicylic acid and camphosulfonic acid.

The physical separation of the two ethers may be effected by crystallization from a solvent or by chromatography, preferably by chromatography over silica gel. The acid hydrolysis of the ether is preferably effected with p-toluene sulfonic acid. The alcohol may be purified by chromatography over silica gel and elution with a 9–1 benzene-ethyl acetate mixture to obtain (S) α-cyano-3-phenoxy-benzyl alcohol with a specific rotation of $[\alpha]_D^{20} = -16.5°\pm1.5°$ (c=0.8% in benzene).

(S) α-cyano-3-phenoxy-benzyl alcohol is a very useful industrial intermediate since it is known in the field of pyrethrinoid compounds that the cyclopropane carboxylic acid esters of (S) α-cyano-3-phenoxy-benzyl alcohol generally possess a greater insecticidal activity than the esters of the corresponding (R) alcohols. (S) α-cyano-3-phenoxy-benzyl alcohol permits to prepare by simple esterification its ester with 1R, cis 2,2-dimethyl-3-(2',2'-dibromovinyl)-cyclopropane-1-carboxylic acid, a known ester with remarkable insecticidal activity.

The invention includes the novel process for the preparation of (S) α-cyano-3-phenoxy-benzyl 1R, cis 2,2-dimethyl-3-(2',2'-dibromovinyl)-cyclopropane-1-carboxylate by reacting (S) α-cyano-3-phenoxy-benzyl alcohol and 1R, cis 2,2-dimethyl-3-(2',2'-dibromovinyl)-cyclopropane-1-carboxylic acid or a functional derivative thereof in an organic solvent.

Until now, certain esters of (S) α-cyano-3-phenoxy-benzyl alcohol could not be prepared because of the lack of the alcohol with the (S) configuration. For example, it has been impossible to obtain (S) α-cyano-3-phenoxy-benzyl "D"2-isopropyl-2-p-chlorophenyl-acetate. However, because of the present invention, it is now possible to prepare the said ester by esterification of (S) α-cyano-3-phenoxy-benzyl alcohol with "D"2- isopropyl-2-p-chlorophenyl-acetyl chloride which ester possesses excellent insecticidal properties.

The process of the invention allows an advantageously economical preparation of (S) α-cyano-3-phenoxy-benzyl alcohol in an original manner and permits the obtention of very active insecticidal esters of the said alcohol, some of which have not been previously accessible.

The novel intermediate products of the invention are selected from the group consisting of (1R,5S) 6,6-dimethyl-4(R)-[(S)-cyano-(3'-phenoxyphenyl)-methoxy]-3-oxa-bicyclo-(3,1,0)-hexan-2-one and (1R,5S) 6,6-dimethyl-4(R)-[(R)-cyano-(3'-phenoxyphenyl)-methoxy]-3-oxa-bicyclo-(3,1,0)-hexan-2-one and mixtures thereof.

In the following examples there are described several preferred embodiments to illustrate the invention. However, it is to be understood that the invention is not intended to be limited to the specific embodiments.

EXAMPLE 1

(S) α-cyano-3-phenoxy-benzyl alcohol

STEP A: mixture of (1R,5S) 6,6-dimethyl-4(R)-[(S)-cyano-(3'-phenoxyphenyl)-methoxy]-3-oxa-bicyclo-(3,1,0)-hexan-2-one and (1R,5S) 6,6-dimethyl-4(R)-[(R)-cyano-(3'-phenoxyphenyl)-methoxy]-3-oxa-bicyclo-(3,1,0)-hexan-2-one A mixture of 22.5 g of (R,S) α-cyano-3-phenoxy-benzyl alcohol, 9.46 g of the lactone of cis 2,2-dimethyl-3S-(dihydroxymethyl)-cyclopropane-1R-carboxylic acid and 0.150 g of p-toluene sulfonic acid was heated at 80° C. at a pressure of $10^{-2}$ mm Hg for 2 hours while distilling off the water of reaction and the mixture was then cooled to 20° C. to obtain 30.70 g of raw mixture A containing (1R,5S) 6,6-dimethyl-4(R)-[(S)-cyano-(3'-phenoxyphenyl)-methoxy]-3-oxa-bicyclo (3,1,0)-hexan-2-one and (1R,5S) 6,6-dimethyl-4(R)-[(R)-cyano-(3'-phenoxyphenyl)-methoxy]-3-oxa-bicyclo-(3,1,0)-hexan-2-one with unreacted starting materials as the principal impurity.

STEP B: (1R,5S) 6,6-dimethyl-4(R)-[(S)-cyano-(3'-phenoxyphenyl)-methoxy]-3-oxa-bicyclo-(3,1,0)-hexan-2-one Mixture A from Step A was chromatographed over silica gel and elution with a 95-5 benzene-ethyl acetate mixture yielded 10.9 g of (1R,5S) 6,6-dimethyl-4(R)-[(S)-cyano-(3'-phenoxyphenyl)-methoxy]-3-oxa-bicyclo-(3,1,0)-hexan-2-one melting at 126° C. and having a specific rotation of $[\alpha]_D^{20} = -71°$ (c=1% in benzene).

| U.V. Spectrum (ethanol): | |
| --- | --- |
| Inflexion at 226 nm | $E_1^1 = 319$ |
| Inflexion towards 267 nm | $E_1^1 = 52$ |
| Inflex. towards 271 nm | $E_1^1 = 56$ |
| Maximum at 276 nm | $E_1^1 = 60$ |
| Inflexion towards 280 nm | $E_1^1 = 48$ |

Circular Dichroism (dioxane):
Δε = −4.2 at 225 nm (max.)
Δε = +0.39 at 287 nm (max.)
RMN Spectrum (deuterochloroform):
Peaks at 1.18–1.23 ppm (hydrogens of geminal methyls); at 1.98–2.08 ppm and 2.15–2.25 ppm (hydrogens of cyclopropyl); at 5.53–5.56 ppm (hydrogen on carbon to which —CN is attached and 4-hydrogen); at 6.91–7.25 ppm (hydrogens of aromatic ring).

STEP C: (S) α-cyano-3-phenoxy-benzyl alcohol 1 g of p-toluene sulfonic acid monohydrate was added to a mixture of 10 g of the product of Step B, 50 ml of water and 100 ml of dioxane and the mixture was refluxed for 23 hours and was then evaporated under reduced pressure to half its original volume, Ether was added to the mixture with stirring and the decanted organic phase was washed with water, dried and evaporated to dryness under reduced pressure. The 9.5 g of residue was chromatographed over silica gel and was eluted with a 9-1 benzene ethyl acetate mixture to obtain 6.1 g of (S) α-cyano-3-phenoxy-benzyl alcohol with a specific rotation of $[\alpha]_D^{20} = -16.5° \pm 1.5°$ (c=0.8% in benzene).

RMN Spectrum (deuterochloroform):
Peaks at 3.25 ppm (hydrogen of alcohol group); at 5.42 ppm (hydrogen of carbon attached to —CN).

EXAMPLE 2

(S) α-cyano-3-phenoxy-benzyl D 2-isopropyl-2-p-chlorophenyl-acetate

STEP A: (+) α-phenylethylamine L 2-isopropyl-2-p-chlorophenyl-acetate 140 g of (+) α-phenylethylamine were added with stirring to a mixture of 250 g of DL 2-isopropyl-2-p-chlorophenyl-acetic acid in 4 liter of ethanol containing 70% by volume of water during which precipitation occured and the mixture was heated to reflux. Sufficient ethanol containing 70% water was added to the refluxing mixture to effect total dissolution (about 3.25 liters) and the mixture was slowly cooled. Crystallization began at about 65° C. and the mixture was stirred at 20° C. for 48 hours. The mixture was vacuum filtered and the recovered product was washed with ethanol to obtain 188.9 g of raw (+) α-phenylethylamine L 2-isopropyl-2-p-chlorophenyl-acetate with a specific rotation of $[\alpha]_D^{20} = +3.5°$ (c=0.5% in methanol). The raw product was added to 4 liters of ethanol containing 70% by volume of water and while heating the mixture at reflux 2 more liters of the solvent were added to effect total dissolution. The mixture was cooled to 20° C. and was stirred at 20° C. for 20 hours and was then vacuum filtered. The recovered product was washed and dried to obtain 147.9 g of the desired salt with a melting point of 210° C. (with decomposition) and having a specific rotation of $[\alpha]_D^{20} = +4.5°$ (c=0.8% in ethanol)

STEP B:

The combined mother liquors from the resolution and purification of Step A were evaporated to dryness and the residue was suspended in 300 ml of methylene chloride. An aqueous solution of 2 N hydrochloric acid was added to the mixture with stirring to obtain a pH of 1 (about 350 ml added) and the decanted organic phase was removed. The aqueous phase was extracted with methylene chloride and the combined organic phases were washed with water. The wash waters were reextracted with methylene chloride and the combined organic phases were dried and filtered. The filtrate was evaporated to dryness under reduced pressure to obtain 153.7 g of a mixture of D 2-isopropyl-2-p-chlorophenyl-acetic acid and DL 2-isopropyl-2-p-chlorophenyl-acetic acid.

STEP C: (−) α-phenylethylamine D 2-isopropyl-2-p-chlorophenyl-acetate 86 g of (−) α-phenylethylamine were added over 15 minutes to a mixture of 153 g of the product of Step B and 4 liters of ethanol containing 70% by volume of water and the mixture was refluxed while adding sufficient additional solvent to obtain total dissolution (about 2.25 liters). The mixture was slowly cooled and was then stirred at 20° C. for 20 hours. The mixture was vacuum filtered and the recovered product was washed with ethanol and dried to obtain 168.2 g of raw (−) α-phenylethylamine D 2-isopropyl-2-parachlorophenylacetate with a specific rotation of $[\alpha]_D^{20} = -5°$ (c=0.6% in methanol). 168 g of the product were added to 4 liters of ethanol containing 70% by volume of water and the mixture was refluxed while adding 1.5 liters of the solvent to obtain total dissolution. The mixture was allowed to cool to 20° C. and was then stirred at 20° C. for 48 hours and was vacuum filtered. The recovered product was washed with ethanol and dried to obtain 143.1 g of the desired salt melting at 210° (with decomposition) and having a specific rotation of $[\alpha]_D^{20} = -5°$ (c=0.8% in methanol).

STEP D: D 2-isopropyl-2-p-chlorophenyl-acetic acid 286 ml of 2 N aqueous hydrochloric acid were added with stirring to a mixture of 143 g of the product of Step C and 286 ml of methylene chloride and the mixture was stirred for 15 minutes resulting in 2 limpid phases. The decanted aqueous phase was extracted with methylene chloride and the combined organic phases were washed with water. The aqueous wash waters were extracted with methylene chloride and the organic phases were dried and filtered. The filtrate was evaporated to dryness to obtain 91 g of D 2-isopropyl-2-p-chlorophenyl-acetic acid melting at 105° C. and having a specific rotation of $[\alpha]_D^{20} = +42°$ (c=1% in ethanol).

STEP E: D 2-isopropyl-2-p-chlorophenyl acetyl chloride 10 g of the product of Step D were added to a mixture of 50 ml of petroleum ether (b.p.=35°–70° C.) and 20 ml of thionyl chloride and the mixture was refluxed for 4 hours and was then cooled. The mixture was evaporated to dryness to obtain 10.8 g of D 2-isopropyl-2-p-chlorophenyl acetyl chloride.

STEP F: (S) α-cyano-3-phenoxy-benzyl D 2-isopropyl-2-p-chlorophenyl-acetate

A mixture of 3 g of (S) α-cyano-3-phenoxy-benzyl alcohol, 3.1 g of the product of Step E and 50 ml of benzene was cooled to 15° C. and then a mixture of 4 ml of pyridine and 10 ml of benzene was added thereto dropwise. The mixture was stirred at 20° C. for 2 hours and was then poured into 2 N aqueous hydrochloric acid solution. The decanted organic phase was dried and filtered and the filtrate was evaporated to dryness under reduced pressure. The residue was chromatographed over silica gel and was eluted with benzene to obtain 4.4 g of (S) α-cyano-3-phenoxy-benzyl D 2-isopropyl-2-p-chlorophenyl-acetate with a specific rotation of $[\alpha]_D^{20} = +13.5°$ (c=2% in benzene) in the form of long crystals melting at 62° C.

Analysis: $C_{25}H_{22}ClNO_3$; molecular weight=419.88.
Calculated: %C 71.50; %H 5.28; %Cl 8.44; %N 3.34.
Found: %C 71.4; %H 5.3; %Cl 9.1; %N 3.3.
Circular Dichroism (dioxane):
$\Delta\epsilon = +0.1$ at 253 nm (max.)
$\Delta\epsilon = +0.23$ at 277 nm (max.)
$\Delta\epsilon = +0.27$ at 282 nm (max.)
$\Delta\epsilon = +0.27$ at 286 nm (max.)
RMN Spectrum (deuterochloroform):

Peaks at 0.63–0.75 ppm and 0.88–1.0 ppm (hydrogens of methyls of isopropyl); at 2.25 ppm (isopropyl hydrogen attached to carbon α-to asymetric carbon); at 3.17–3.33 ppm (hydrogen on asymetrical carbon of acid); at 6.4 ppm (hydrogen of carbon α to —CN); at 6.91–7.25 ppm (hydrogens of aromatic ring).

EXAMPLE 3

(S) α-cyano-3-phenoxy-benzyl 1R, cis 2,2-dimethyl-3-(2',2'-dibromovinyl)-cyclopropane-1-carboxylate A solution of 1.25 g of 2,2-dimethyl-3-(2',2'-dibromovinyl)-cyclopropane-1-carboxylic acid chloride in 2 ml of toluene was slowly added to a solution of 640 mg of (S) α-cyano-3-phenoxy-benzyl alcohol in 10 ml of anhydrous toluene at −10° C. and then a solution of 0.5 ml of pyridine in 2 ml of toluene was added thereto. The mixture was held at 20° C. for 2 hours and then 48 hours at 0° C. and was then washed with dilute hydrochloric acid, then with a sodium bicarbonate solution, was dried and evaporated to dryness to obtain 2.1 g of product. The said product was chromatographed over silica gel and was eluted with a 9–1 petroleum ether-ether mixture to obtain 1.3 g of pure (S) α-cyano-3-phenoxy-benzyl 1R, cis 2,2-dimethyl-3-(2',2'-dibromovinyl)-cyclopropane-1-carboxylate melting at 100° C. and having a specific rotation of $[\alpha]_D^{20} = +19°$ (c=0.8% in CHCl₃).

Various modifications of the process and product of the invention may be made without departing from the spirit or scope thereof and it should be understood that the invention is intended to be limited only as defined in the appended claims.

We claim:

1. (S) α-cyano-3-phenoxy-benzyl alcohol of the formula

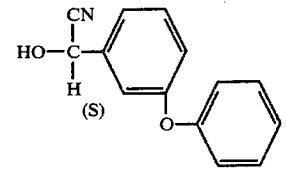

free of its (R) form.

2. The alcohol of claim 1 with a specific rotation of $[\alpha]_D^{20} = -16.5° \pm 1.5°$ (c=0.8% in benzene).

* * * * *